(12) United States Patent
Karmarkar et al.

(10) Patent No.: US 9,423,475 B2
(45) Date of Patent: Aug. 23, 2016

(54) ELECTRICAL LEAD ASSEMBLIES FOR MRI-COMPATIBLE MEDICAL DEVICES AND MRI-COMPATIBLE MEDICAL DEVICES INCORPORATING SAME

(71) Applicant: MRI Interventions, Inc., Memphis, TN (US)

(72) Inventors: Parag Karmarkar, Columbia, MD (US); Rajesh Pandey, Irvine, CA (US)

(73) Assignee: MRI Interventions, Inc., Memphis, TN (US)

( * ) Notice: Subject to any disclaimer, the term of this patent is extended or adjusted under 35 U.S.C. 154(b) by 828 days.

(21) Appl. No.: 13/799,588

(22) Filed: Mar. 13, 2013

(65) Prior Publication Data

US 2014/0266207 A1    Sep. 18, 2014

(51) Int. Cl.
*G01R 33/28* (2006.01)
*A61B 18/14* (2006.01)
*A61B 17/00* (2006.01)
*A61B 18/00* (2006.01)

(52) U.S. Cl.
CPC .......... *G01R 33/287* (2013.01); *A61B 18/1492* (2013.01); *A61B 2017/00039* (2013.01); *A61B 2018/00773* (2013.01); *A61B 2018/00815* (2013.01); *A61B 2034/2051* (2016.02)

(58) Field of Classification Search
CPC ... G01R 33/287; A61B 18/1492; A61B 5/055
USPC ................................. 600/410, 420, 422, 423
See application file for complete search history.

(56) References Cited

U.S. PATENT DOCUMENTS

| 6,701,176 | B1 | 3/2004 | Halperin et al. |
| 2009/0118610 | A1* | 5/2009 | Karmarkar .......... A61B 5/0476 600/420 |

FOREIGN PATENT DOCUMENTS

WO    WO 2008/115383 A2    9/2008

* cited by examiner

*Primary Examiner* — Peter Luong
(74) *Attorney, Agent, or Firm* — Myers Bigel & Sibley

(57) ABSTRACT

An elongate electrical lead assembly that reduces localized heating due to MR scanner-induced currents includes a first elongate electrical lead having a series of alternating single layer coil sections and multi-layer coil sections, a second elongate electrical lead having a series of alternating single layer coil sections and multi-layer coil sections, and a third elongate electrical lead having a coiled section that coaxially surrounds the first and second electrical leads. Each multi-layer coil section of the second electrical lead is coiled around a respective single layer coil section of the first electrical lead, and each single layer coil section of the second electrical lead is coiled around a respective multi-layer coil section of the first electrical lead.

23 Claims, 14 Drawing Sheets

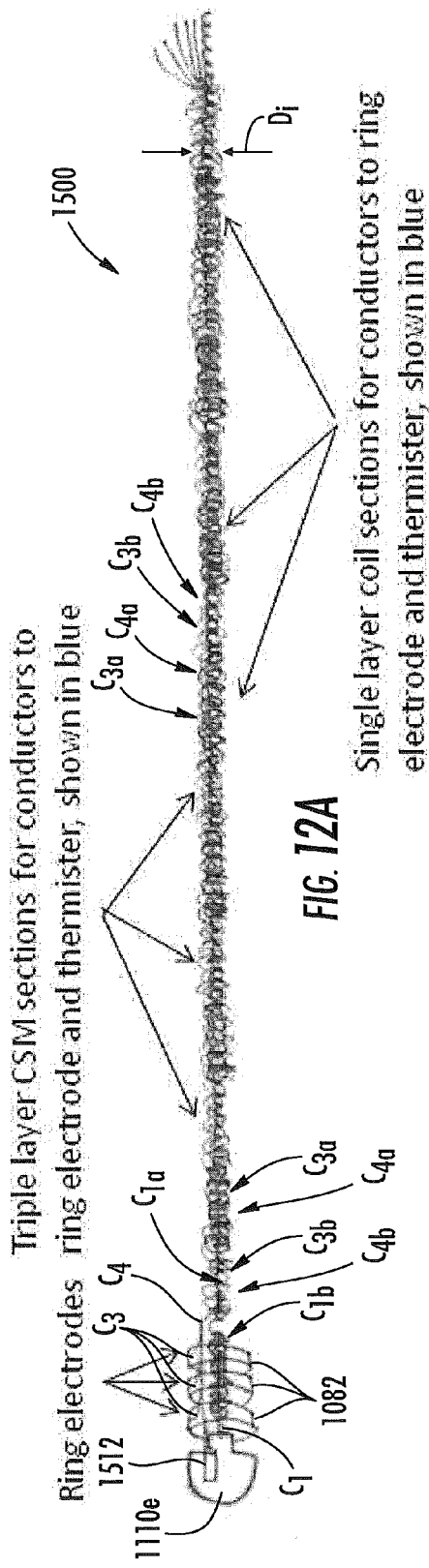
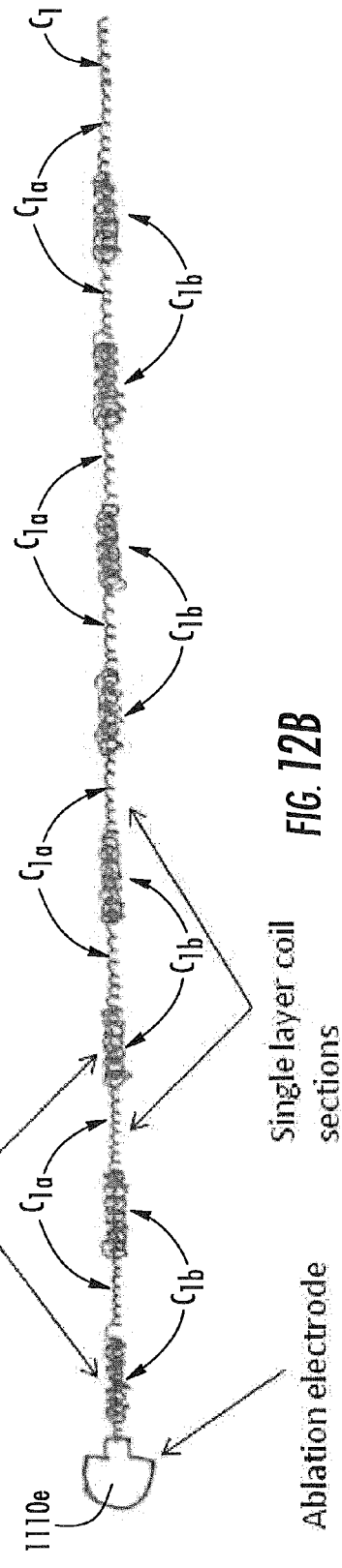
FIG. 12A
FIG. 12B

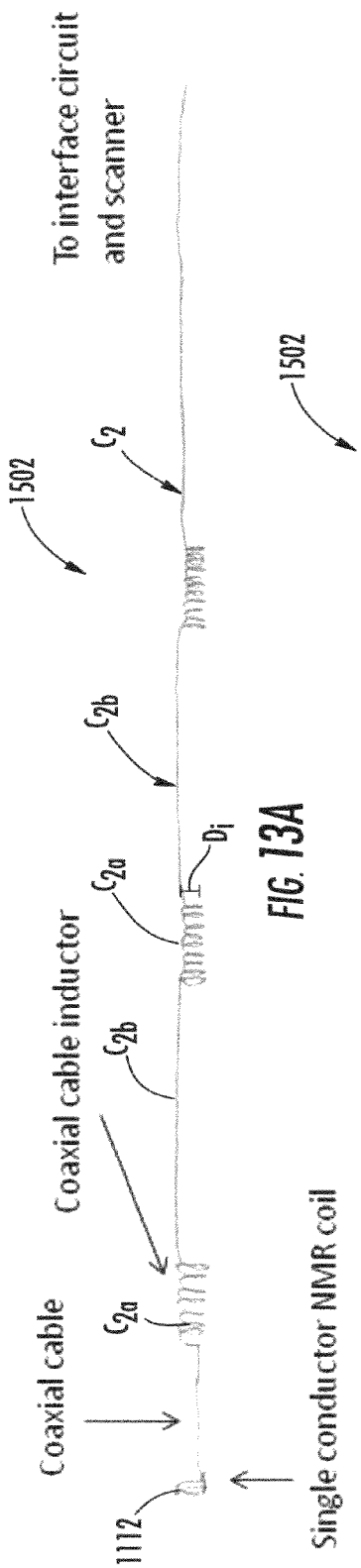
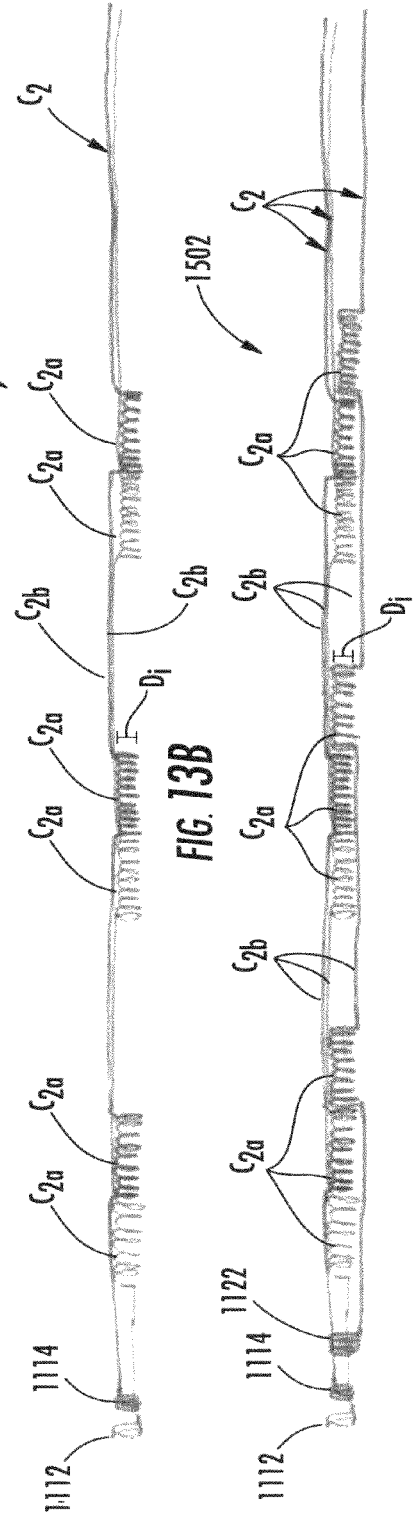
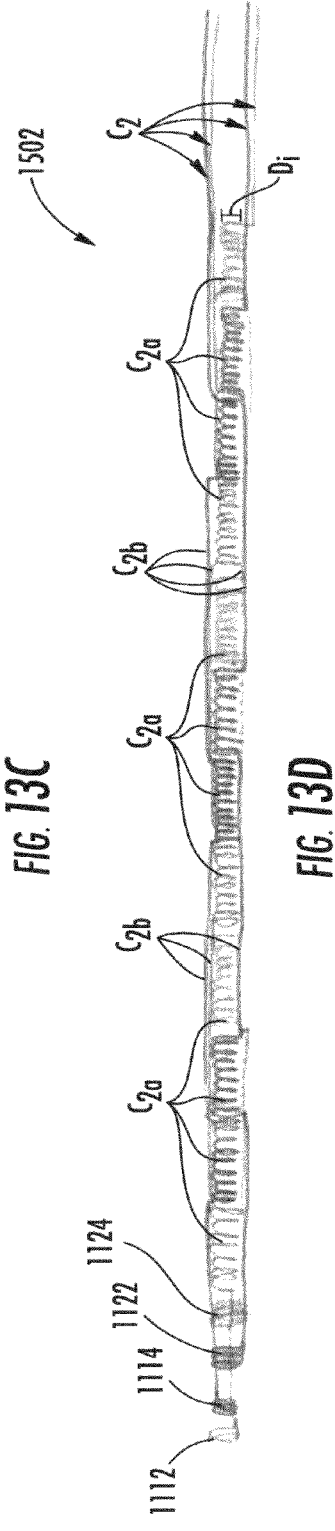
FIG. 13A
FIG. 13B
FIG. 13C
FIG. 13D

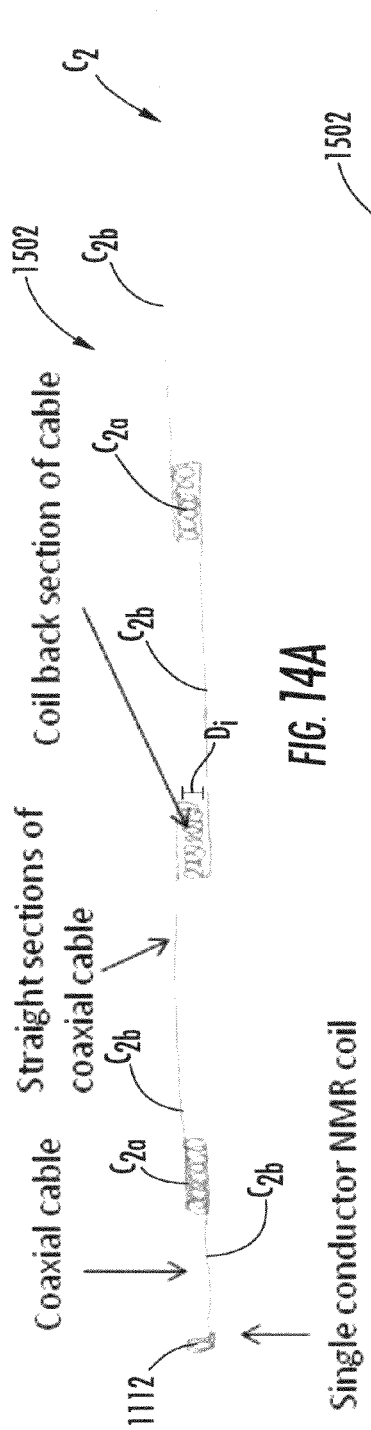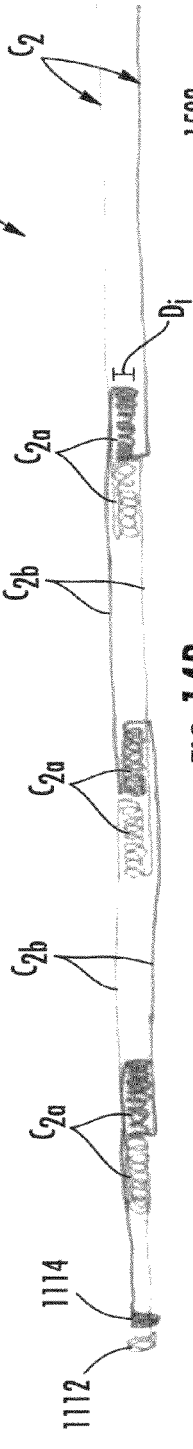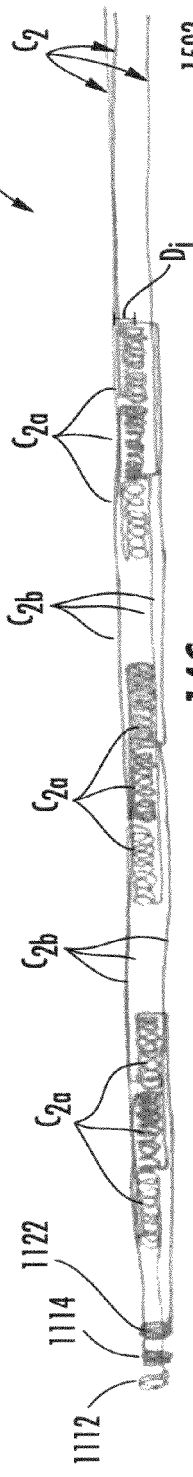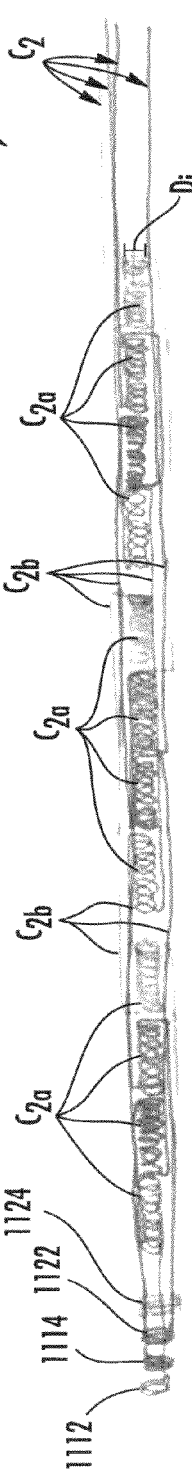
FIG. 14A
FIG. 14B
FIG. 14C
FIG. 14D

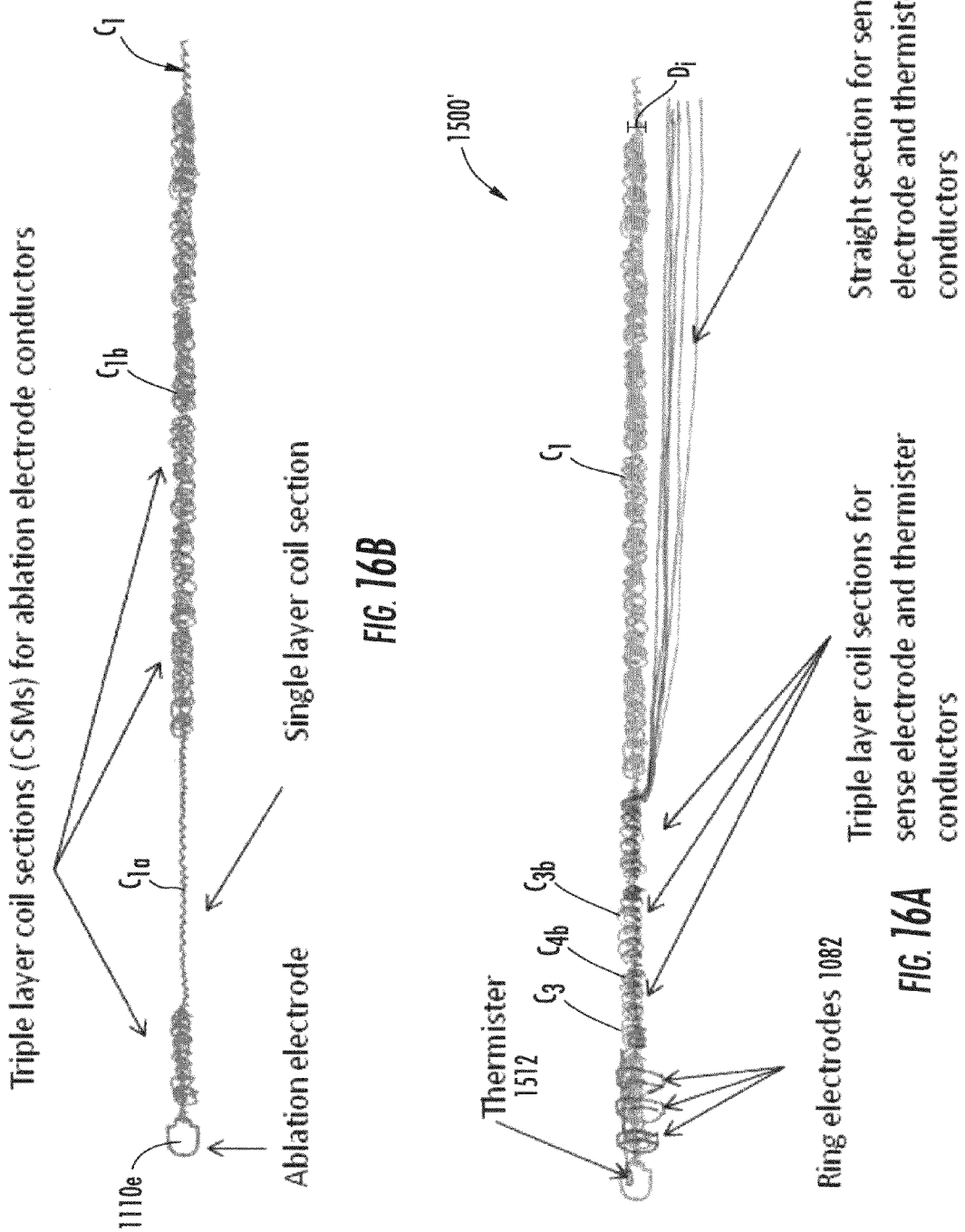

ELECTRICAL LEAD ASSEMBLIES FOR MRI-COMPATIBLE MEDICAL DEVICES AND MRI-COMPATIBLE MEDICAL DEVICES INCORPORATING SAME

FIELD OF THE INVENTION

The present invention relates to MRI-guided systems and may be particularly suitable for MRI-guided cardiac systems such as EP systems for treating Atrial Fibrillation (AFIB).

BACKGROUND

Heart rhythm disorders (arrhythmias) occur when there is a malfunction in the electrical impulses to the heart that coordinate how the heart beats. During arrhythmia, a heart may beat too fast, too slowly or irregularly. Catheter ablation is a widely used therapy for treating arrhythmias and involves threading a catheter through blood vessels of a patient and into the heart. In some embodiments, radio frequency (RF) energy may be applied through the catheter tip to destroy abnormal heart tissue causing the arrhythmia. In other embodiments a catheter tip may be configured to cryogenically ablate heart tissue.

Guiding the placement of a catheter during ablation therapy within the heart is important. Conventional catheter ablation procedures are conducted using X-ray and/or ultrasound imaging technology to facilitate catheter guidance and ablation of heart tissue. Conventional Cardiac EP (Electro-Physiology) Systems are X-ray based systems which use electroanatomical maps. Electroanatomical maps are virtual representations of the heart showing sensed electrical activity. Examples of such systems include the Carto® electroanatomic mapping system from Biosense Webster, Inc., Diamond Bar, Cali., and the EnSite NavX® system from Endocardial Solutions Inc., St. Paul, Minn.

Magnetic resonance imaging (MRI) has several distinct advantages over X-ray imaging technology, such as excellent soft-tissue contrast, the ability to define any tomographic plane, and the absence of ionizing radiation exposure. In addition, MRI offers several specific advantages that make it especially well suited for guiding various devices used in diagnostic and therapeutic procedures including: 1) real-time interactive imaging, 2) direct visualization of critical anatomic landmarks, 3) direct high resolution imaging, 4) visualization of a device-tissue interface, 5) the ability to actively track device position in three-dimensional space, and 6) elimination of radiation exposure.

Induced RF currents (referred to as RF coupling) on coaxial cables, electrical leads, guide wires, and other elongated devices utilized in MRI environments can be problematic. Such RF coupling may cause significant image artifacts, and may induce undesired RF energy deposition in the tissue in contact/adjacent with the device, resulting in local tissue heating and permanent tissue damage.

SUMMARY

It should be appreciated that this Summary is provided to introduce a selection of concepts in a simplified form, the concepts being further described below in the Detailed Description. This Summary is not intended to identify key features or essential features of this disclosure, nor is it intended to limit the scope of the invention.

According to some embodiments of the present invention, an elongate electrical lead subassembly for use in MRI-compatible medical devices and that reduces localized tissue heating due to MR scanner-induced RF currents in these devices includes at least one first conductor (which may include a plurality of conductors, individually insulated) comprising a series of alternating single layer coil sections and multi-layer coil sections and attached at one end portion to an ablation electrode, and at least one second conductor (which may include a plurality of conductors, individually insulated) comprising a series of alternating single layer coil sections and multi-layer coil sections and attached at one end portion to a sensing electrode upstream of the ablation electrode. Each multi-layer coil section of the at least one second conductor is coiled around a respective single layer coil section of the at least one first conductor, and each single layer coil section of the at least one second conductor is coiled around a respective multi-layer coil section of the at least one first conductor such that the electrical lead subassembly has a substantially constant diameter along at least a segment of its length. The at least one first conductor and the at least one second conductor are insulated conductors. In some embodiments, the at least one first and second conductors are coaxial cables.

In some embodiments, the multi-layer coil sections of the at least one first conductor and the at least one second conductor have an impedance greater than about 50 ohms per centimeter at a nuclear magnetic resonance (NMR) operating frequency of an MRI scanner.

In some embodiments, the multi-layer coil sections of the at least one first conductor and at least one second conductor include a first coiled layer that extends in a first lengthwise direction for a first physical length, a second coiled layer coiled around the first coiled layer in a substantially opposing lengthwise direction for a second physical length, and a third coiled layer coiled around the second coiled layer in the first lengthwise direction for a third physical length. In some embodiments, coils in at least two of the first, second and third coil layers of the at least one first conductor have a different pitch. In some embodiments, coils in at least two of the first, second and third coil layers of the at least one first conductor have the same pitch.

According to some embodiments of the present invention, an elongate electrical lead subassembly for use in MRI-compatible medical devices that reduces localized tissue heating due to MR scanner-induced currents includes a plurality of conductors, each conductor having a series of alternating straight sections and coiled sections. The conductors are arranged such each coiled section of a conductor is in adjacent, axial relationship with a respective coiled section of another conductor, and each conductor is attached at one end portion to an RF tracking coil.

According to some embodiments of the present invention, an elongate electrical lead assembly for use in MRI-compatible medical devices includes a first elongate electrical lead subassembly comprising at least one conductor (which may include a plurality of conductors, individually insulated) having a series of alternating single layer coil sections and multi-layer coil sections and connected at one end portion to an ablation electrode, a second elongate electrical lead subassembly comprising at least one conductor (which may include a plurality of conductors, individually insulated) having a series of alternating single layer coil sections and multi-layer coil sections and connected at one end portion to a sensing electrode upstream of the ablation electrode, and a third elongate electrical lead comprising at least one conductor (which may include a plurality of conductors, individually insulated) having a coiled section that coaxially surrounds the first and second electrical leads and connected at one end portion to an RF tracking coil. Each multi-layer coil section of the second electrical lead subassembly is coiled around a respective single layer coil section of the first electrical lead subassembly, and each single layer coil section of the second electrical lead subassembly is coiled around a respective multi-layer coil section of the first electrical lead subassembly.

In some embodiments, the third electrical lead includes a plurality of conductors, and the coiled sections of the conductors are in adjacent, axial relationship with each other.

In some embodiments, the multi-layer coil sections of the first and second electrical lead subassemblies each include a first coiled layer that extends in a first lengthwise direction for a first physical length, a second coiled layer coiled around the first coiled layer in a substantially opposing lengthwise direction for a second physical length, and a third coiled layer coiled around the second coiled layer in the first lengthwise direction for a third physical length.

In some embodiments, the coiled section of the third electrical lead subassembly includes coils wound right to left. In some embodiments, the coiled section of the third electrical lead includes coils wound left to right.

In some embodiments, the multi-layer coil sections of the first and second electrical lead subassemblies have an impedance greater than about 50 ohms per centimeter at a nuclear magnetic resonance (NMR) frequency.

In some embodiments, the electrical lead assembly includes a fourth electrical lead subassembly having a series of alternating single layer coil sections and multi-layer coil sections and connected at one end portion to a thermistor. Each multi-layer coil section of the fourth electrical lead subassembly is coiled around a respective single layer coil section of the first electrical lead subassembly, and each single layer coil section of the fourth electrical lead subassembly is coiled around a respective multi-layer coil section of the first electrical lead subassembly.

According to other embodiments of the present invention, an MRI-compatible medical device that reduces localized tissue heating due to MR scanner-induced currents includes an elongated flexible shaft having a distal end portion, and an opposite proximal end portion, an ablation electrode at the flexible shaft distal end portion, at least one sensing electrode at the shaft distal end portion, and an electrical connector interface, for example, proximate the flexible shaft proximal end portion. A first elongate electrical lead extends longitudinally within the flexible shaft and has opposing proximal and distal end portions. The first electrical lead distal end portion is connected to the ablation electrode and the first electrical lead proximal end is connected to the electrical connector interface. The first electrical lead includes a series of alternating single layer coil sections and multi-layer coil sections. A second elongate electrical lead extends longitudinally within the flexible shaft and has opposing proximal and distal end portions. The second electrical lead distal end portion is connected to the at least one sensing electrode, and the second electrical lead proximal end is connected to the electrical connector interface. The second electrical lead includes a series of alternating single layer coil sections and multi-layer coil sections. Each multi-layer coil section of the second electrical lead is coiled around a respective single layer coil section of the first electrical lead, and each single layer coil section of the second electrical lead is coiled around a respective multi-layer coil section of the first electrical lead. The at least one conductors of the first and second electrical leads are individually insulated and, in some embodiments, may be coaxial cables.

In some embodiments, the multi-layer coil sections of the first and second electrical leads include a first coiled layer that extends in a first lengthwise direction for a first physical length, a second coiled layer coiled around the first coiled layer in a substantially opposing lengthwise direction for a second physical length, and a third coiled layer coiled around the second coiled layer in the first lengthwise direction for a third physical length. In some embodiments, coils in at least two of the first, second and third coil layers of the first electrical lead have a different pitch. In some embodiments, coils in at least two of the first, second and third coil layers of the first electrical lead have the same pitch.

In some embodiments, the multi-layer coil sections of the first and second electrical leads have an impedance greater than about 50 ohms per centimeter at a nuclear magnetic resonance (NMR) frequency.

In some embodiments, the medical device includes at least one RF tracking coil positioned adjacent the distal end portion of the flexible shaft. A third elongate electrical lead extends longitudinally within the flexible shaft and has opposing proximal and distal end portions. The third electrical lead distal end portion is connected to the at least one RF tracking coil, and the third electrical lead proximal end is connected to the electrical connector interface. The third electrical lead includes a first coiled section that coaxially surrounds the first and second electrical leads. In some embodiments, the at least one RF tracking coil includes a plurality of RF tracking coils, and the third electrical lead at least one conductor comprises a respective plurality of conductors having coiled sections in adjacent, axial relationship with each other.

In some embodiments, the medical device includes a thermistor positioned adjacent the distal end portion of the flexible shaft. A fourth electrical lead extends longitudinally within the flexible shaft and has opposing proximal and distal end portions. The fourth electrical lead distal end portion is connected to the thermistor and the fourth electrical lead proximal end is connected to the electrical connector interface. The fourth electrical lead includes a series of alternating single layer coil sections and multi-layer coil sections. Each multi-layer coil section of the fourth electrical lead is coiled around a respective single layer coil section of the first electrical lead, and each single layer coil section of the fourth electrical lead is coiled around a respective multi-layer coil section of the first electrical lead.

According to other embodiments of the present invention, an elongate electrical lead assembly for use in MRI-compatible medical devices includes a first elongate electrical lead having at least one conductor with first and second multi-layer coil sections with a single layer coil section therebetween, and a second elongate electrical lead having at least one conductor with at least one multi-layer coil section. The first multi-layer coil section has a length greater than a length of the second multi-layer coil section and greater than a length of the single layer coil section. The at least one multi-layer coil section of the second electrical lead is coiled around the single layer coil section of the first electrical lead. A third elongate electrical lead having at least one conductor with a coiled section coaxially surrounds the first and second electrical leads. In some embodiments, the third electrical lead includes a plurality of conductors, and the coiled sections of the conductors are in adjacent, axial relationship with each other.

In some embodiments, the electrical lead assembly includes a fourth electrical lead having at least one multi-layer coil section. The at least one multi-layer coil section of the fourth electrical lead is coiled around the single layer coil section of the first electrical lead.

In some embodiments, the at least one multi-layer coil section of the first and second electrical leads includes a plurality of adjacent multi-layer coil sections. Each multi-layer coil section has a first coiled layer that extends in a first lengthwise direction for a first physical length, a second coiled layer coiled around the first coiled layer in a substantially opposing lengthwise direction for a second physical length, and a third coiled layer coiled around the second coiled layer in the first lengthwise direction for a third physical length.

It is noted that aspects of the invention described with respect to one embodiment may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail below.

BRIEF DESCRIPTION OF THE DRAWINGS

FIG. 12A is a schematic color illustration of an electrical lead subassembly that includes conductors for an ablation electrode, sensing electrodes, and a thermistor/thermocouple of an MRI-compatible medical device, according to some embodiments of the present invention.

FIG. 12B is a schematic color illustration of an ablation electrode conductor in the electrical lead subassembly of FIG. 12A.

FIGS. 13A-13D are schematic color illustrations of alternate RF tracking coil electrical lead subassemblies for an MRI-compatible medical device, according to some embodiments of the present invention. FIG. 13A illustrates a single conductor for a single RF tracking coil; FIG. 13B illustrates two conductors for two RF tracking coils; FIG. 13C illustrates three conductors for three RF tracking coils; and FIG. 13D illustrates four conductors for four RF tracking coils.

FIGS. 14A-14D are schematic color illustrations of further alternate RF tracking coil electrical lead subassemblies, according to some embodiments of the present invention. FIG. 14A illustrates a single conductor for a single RF tracking coil; FIG. 14B illustrates two conductors for two RF tracking coils; FIG. 14C illustrates three conductors for three RF tracking coils; and FIG. 14D illustrates four conductors for four RF tracking coils.

FIG. 16A is a schematic color illustration of an electrical lead subassembly that includes conductors for an ablation electrode, sensing electrodes, and a thermistor/thermocouple of an MRI-compatible medical device, according to some embodiments of the present invention.

FIG. 16B is a schematic color illustration of an ablation electrode conductor in the electrical lead subassembly of FIG. 16A.

DETAILED DESCRIPTION

Figure 1:
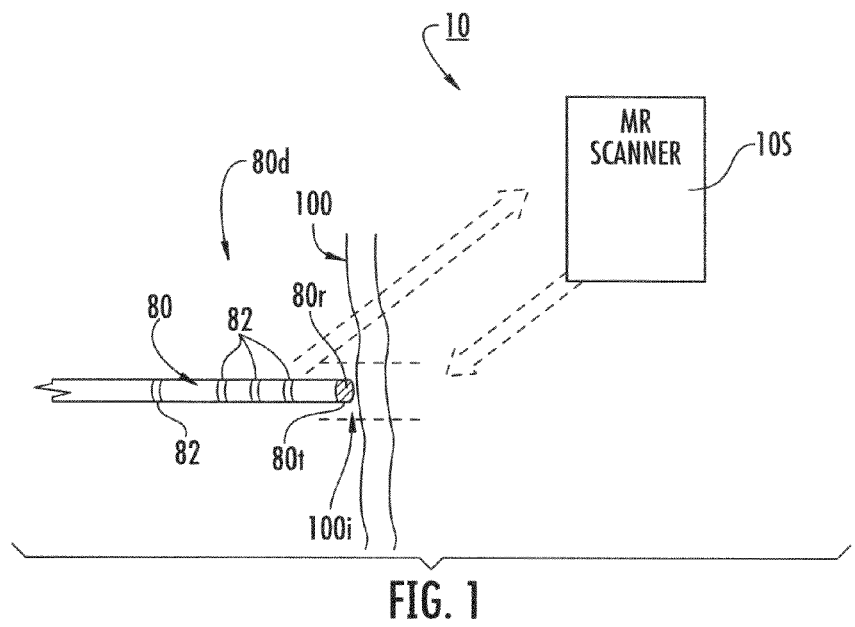
FIG. 1 is a schematic illustration of an MRI-guided system configured to show a device tissue interface using near RT MRI data.

The present invention will now be described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout. It will be appreciated that although discussed with respect to a certain embodiment, features or operation of one embodiment can apply to others.

In the drawings, the thickness of lines, layers, features, components and/or regions may be exaggerated for clarity and broken lines (such as those shown in circuit or flow diagrams) illustrate optional features or operations, unless specified otherwise. In addition, the sequence of operations (or steps) is not limited to the order presented in the claims unless specifically indicated otherwise.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when a feature, such as a layer, region or substrate, is referred to as being "on" another feature or element, it can be directly on the other element or intervening elements may also be present. In contrast, when an element is referred to as being "directly on" another feature or element, there are no intervening elements present. It will also be understood that, when a feature or element is referred to as being "connected" or "coupled" to another feature or element, it can be directly connected to the other element or intervening elements may be present. In contrast, when a feature or element is referred to as being "directly connected" or "directly coupled" to another element, there are no intervening elements present. Although described or shown with respect to one embodiment, the features so described or shown can apply to other embodiments.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of "over" and "under". The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

The term "about", as used herein with respect to a value or number, means that the value or number can vary by +/−twenty percent (20%).

The terms "MRI or MR Scanner" are used interchangeably to refer to a Magnetic Resonance Imaging system and includes the magnet, the operating components, e.g., RF amplifier, gradient amplifiers and operational circuitry including, for example, processors (the latter of which may be held in a control cabinet) that direct the pulse sequences, select the scan planes and obtain MR data. Embodiments of the present invention can be utilized with any MRI Scanner including, but not limited to, GE Healthcare: Signa 1.5T/3.0T; Philips Medical Systems: Achieva 1.5T/3.0T; Integra 1.5T; Siemens: MAGNETOM Avanto; MAGNETOM Espree; MAGNETOM Symphony; MAGNETOM Trio; and MAGNETOM Verio.

The term "near real time" refers to both low latency and high frame rate. Latency is generally measured as the time from when an event occurs to display of the event (total processing time). For tracking, the frame rate can range from between about 100 fps to the imaging frame rate. In some embodiments, the tracking is updated at the imaging frame rate. For near 'real-time' imaging, the frame rate is typically between about 1 fps to about 20 fps, and in some embodiments, between about 3 fps to about 7 fps. The low latency required to be considered "near real time" is generally less than or equal to about 1 second. In some embodiments, the latency for tracking information is about 0.01 s, and typically between about 0.25-0.5 s when interleaved with imaging data. Thus, with respect to tracking, visualizations with the location, orientation and/or configuration of a known intrabody device can be updated with low latency between about 1 fps to about 100 fps. With respect to imaging, visualizations using near real time MR image data can be presented with a low latency, typically within between about 0.01 ms to less than about 1 second, and with a frame rate that is typically between about 1-20 fps. Together, the system can use the tracking signal and image signal data to dynamically present anatomy and one or more intrabody devices in the visualization in near real-time. In some embodiments, the tracking signal data is obtained and the associated spatial coordinates are determined while the MR image data is obtained and the resultant visualization(s) with the intrabody device (e.g., stylet) and the near RT MR image(s) are generated.

The term "RF safe" means that the catheter and any (conductive) lead is configured to operate safely when exposed to RF signals, particularly RF signals associated with MRI systems, without inducing unplanned current that inadvertently unduly heats local tissue or interferes with the planned therapy. The term "MRI visible" means that the device is visible, directly or indirectly, in an MRI image. The visibility may be indicated by the increased SNR of the MRI signal proximate the device. The device can act as an MRI transmit/receive or receive antenna to collect signal from local tissue and/or the device actually generates MRI signal itself, such as via suitable medical grade hydro-based coatings, fluid (e.g., aqueous fluid) filled channels or lumens. The term "MRI compatible" means that the so-called component(s) is safe for use in an MRI environment and as such is typically made of a non-ferromagnetic MRI compatible material(s) suitable to reside and/or operate in a high magnetic field environment. The term "high-magnetic field" refers to field strengths above about 0.5T (Tesla), typically above 1.0T, and more typically between about 1.5T and 10T. Embodiments of the invention may be particularly suitable for 1.5T and/or 3.0T systems.

The term "intrabody device" is used broadly to refer to any diagnostic or therapeutic medical device including, for example, catheters, needles (e.g., injection, suture, and biopsy), forceps (miniature), knives or other cutting members, ablation or stimulation probes, injection or other fluid delivery cannulas, mapping or optical probes or catheters, sheaths, guidewires, fiberscopes, dilators, scissors, implant material delivery cannulas or barrels, and the like, typically having a size that is between about 5 French to about 12 French, but other sizes may be appropriate.

The term "tracking member", as used herein, includes all types of components that are visible in an MRI image including miniature RF tracking coils, passive markers, and receive antennas. In some embodiments of the present invention a miniature RF tracking coil can be connected to a channel of an MRI Scanner. The MR Scanner can be configured to operate to interleave the data acquisition of the tracking coils with the image data acquisition. The tracking data is acquired in a 'tracking sequence block' which takes about 10 msec (or less). In some embodiments, the tracking sequence block can be executed between each acquisition of image data (the 'imaging sequence block'). So the tracking coil coordinates can be updated immediately before each image acquisition and at the same rate. The tracking sequence can give the coordinates of all tracking coils simultaneously. So, typically, the number of coils used to track a device has substantially no impact on the time required to track them.

MRI has several distinct advantages over X-ray imaging technology, such as: excellent soft-tissue contrast, the ability to define any tomographic plane, and the absence of ionizing radiation exposure. In addition, MRI offers several specific advantages that make it especially well suited for guiding transseptal puncture procedures including: 1) near real-time interactive imaging, 2) direct visualization of critical endocardial anatomic landmarks, 3) direct high resolution imaging of the septum, including the fossa ovalis, 4) visualization of the needle tip-tissue interface, 5) the ability to actively track needle position in three-dimensional space, and 6) elimination of radiation exposure.

Embodiments of the present invention can be configured to guide and/or place diagnostic or interventional devices in an MRI environment (e.g., interventional medical suite) to any desired internal region of a subject of interest, including, in some embodiments, to a cardiac location. The subject can be animal and/or human subjects.

Some embodiments of the invention provide systems that can be used to ablate tissue for treating cardiac arrhythmias, and/or to deliver stem cells or other cardio-rebuilding cells or products into cardiac tissue, such as a heart wall, via a minimally invasive MRI guided procedure while the heart is beating (i.e., not requiring a non-beating heart with the patient on a heart-lung machine).

FIG. 1 illustrates an MRI interventional system 10 with a scanner 10S and a flexible intrabody medical device 80 (e.g., an ablation catheter, mapping catheter, etc.) proximate target tissue 100 at a device-tissue interface 100i. The system 10 can be configured to electronically track the 3-D location of the device 80 in the body and identify and/or "know" the location of the tip portion 80t of the device 80 (e.g., the ablation tip) in a coordinate system associated with the 3-D imaging space. As shown in FIG. 1, the device 80 can include a plurality of spaced apart tracking members 82 on a distal end portion thereof. In a particular embodiment, the device 80 can be an ablation catheter and the tip 80t can include an ablation electrode 80e (typically at least one at a distal end portion of the device). Where used, the electrode 80e can be both a sensing and ablation electrode.

Figure 2:
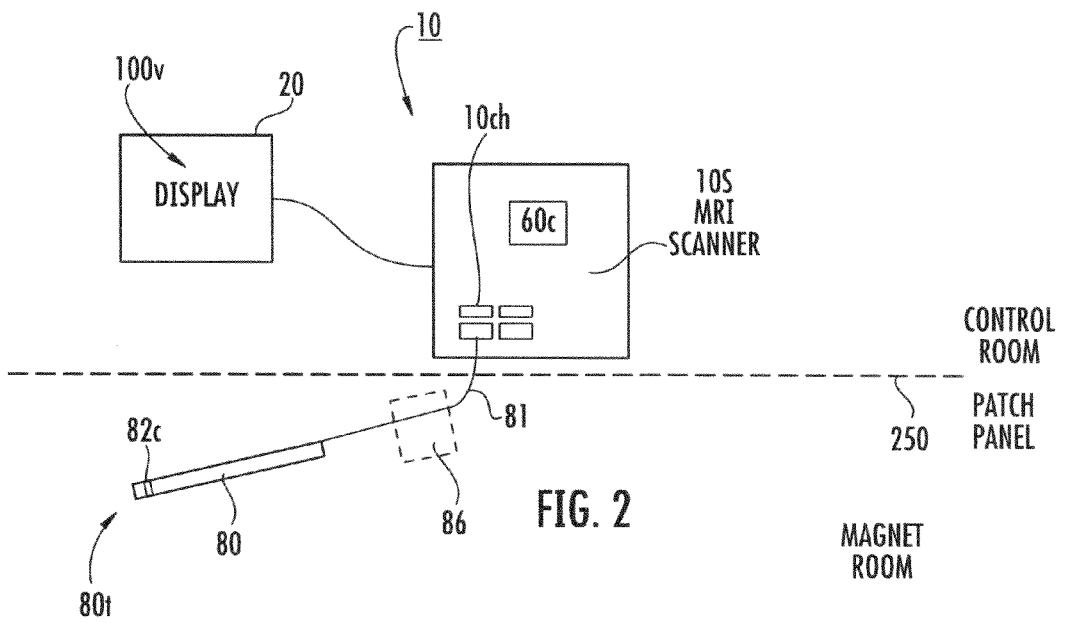
FIG. 2 is a schematic illustration of an intrabody device with a tracking coil electrically connected to a Scanner channel.

The tracking members 82 can comprise miniature tracking coils, passive markers and/or a receive antenna. In a preferred embodiment, the tracking members 82 include at least one miniature tracking coil 82c that is connected to a channel 10ch of an MRI Scanner 10S (FIG. 2). The MR Scanner 10S can be configured to operate to interleave the data acquisition of the tracking coils 82c with the image data acquisition.

Some embodiments of the invention can be utilized with systems that can be used to facilitate ablation of tissue for treating cardiac arrhythmias, or to repair or replace cardiac valves, repair, flush or clean vasculature and/or place stents, and/or to deliver stem cells or other cardio-rebuilding cells or products into cardiac tissue, such as a heart wall, via a minimally invasive MRI guided procedure while the heart is beating (i.e., not requiring a non-beating heart with the patient on a heart-lung machine). The cardiac procedures can be carried out from an inside of the heart or from an outside of the heart. The system may also be suitable for delivering a therapeutic agent or carrying out another treatment or diagnostic evaluation for any intrabody location, including, for example, the brain, gastrointestinal system, genourinary system, spine (central canal, the subarachnoid space or other region), vasculature or other intrabody locations. Additional discussion of exemplary target regions can be found at the end of this document.

The system 10 and/or circuit 60c (FIGS. 2-3) can calculate the position of the tip of the device 80t as well as the shape and orientation of the flexible device based on a priori information on the dimensions and behavior of the device 80 (e.g., for a steerable device, the amount of curvature expected when a certain pull wire extension or retraction exists, distance to tip from different coils 82 and the like). Using the known information of the device 80 and because the tracking signals are spatially associated with the same X, Y, Z coordinate system as the MR image data, the circuit 60c can rapidly generate visualizations showing a physical representation of the location of a distal end portion of the device 80 with near RT MR images of the anatomy.

In some embodiments, the tracking signal data is obtained and the associated spatial coordinates are determined while a circuit 60c in the MRI Scanner 10S (FIG. 2) and/or in communication with the Scanner 10S (FIG. 3) obtains MR image data. The reverse operation can also be used. The circuit 60c can then rapidly render the resultant visualization(s) 100v (see, e.g., FIGS. 5A-5D) with the flexible device(s) 80 shown with a physical representation based on spatial coordinates of the devices in the 3-D imaging space identified using the associated tracking coil data and the near RT MR image(s).

Figure 3:
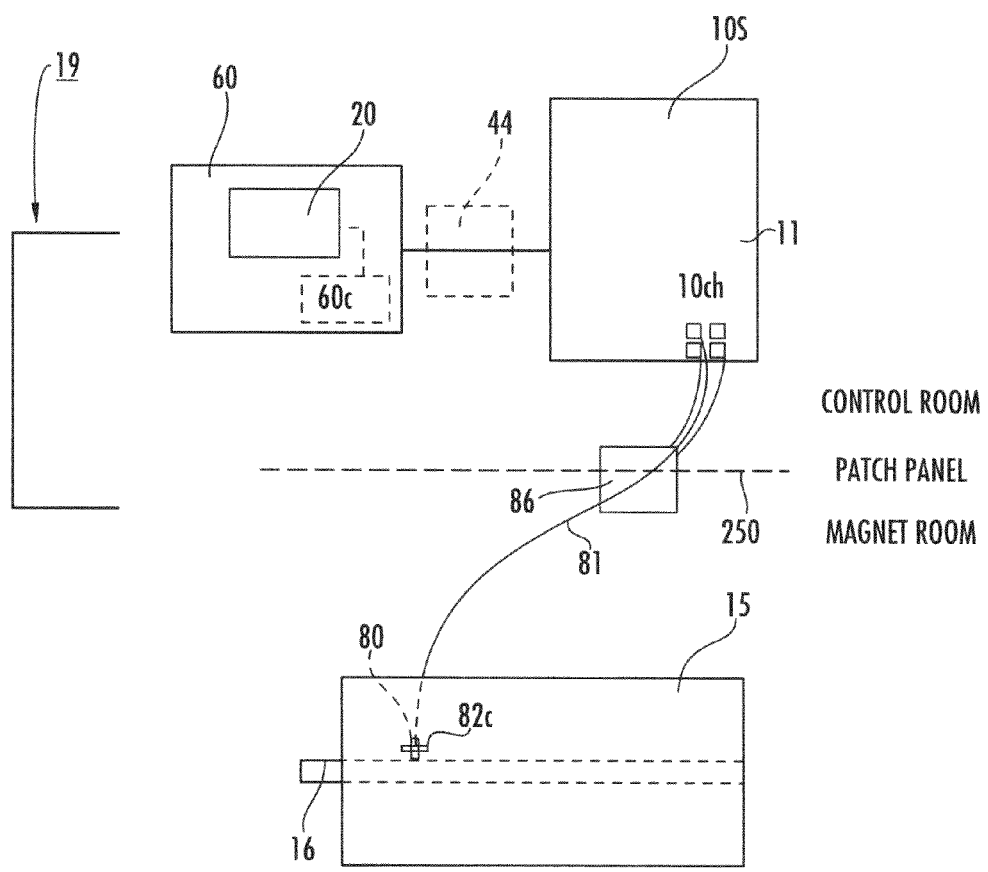
FIG. 3 is a schematic illustration of an MRI system with a workstation and display.

The circuit 60c can be totally integrated into the MR Scanner 10S (e.g., control cabinet), partially integrated into the MR Scanner 10S or be separate from the MR Scanner 10S but communicate therewith. If not totally integrated into the MR Scanner 10S, the circuit 60c may reside partially or totally in a workstation 60 and/or in remote or other local processor(s) and/or ASIC. FIG. 3 illustrates that a clinician workstation 60 can communicate with the MR Scanner 10S via an interface 44. Similarly, the device 80 in the magnet room can connect to the MR Scanner 10S via an interface box 86 which may optionally be integrated into the patch panel 250.

As shown in FIGS. 2 and 3, for example, the system 10 can include at least one (interactive) display 20 in communication with the circuit 60c and/or the Scanner 10S. The display 20 can be configured to display the interactive visualizations 100v. The visualizations 100v can be dynamic showing the movement of the device 80 relative to the intrabody anatomical structure shown by the displayed near-real time MRI image.

FIG. 2 illustrates that the device 80 can include at least one conductor 81, such as a coaxial cable that connects a respective tracking coil 82c to a channel 10ch of the MR Scanner 10S. The MR Scanner 10S can include at least 16 separate channels, and typically more channels but may operate with less as well. Each device 80 can include between about 1-10 tracking coils, typically between about 1-4. The coils 82c on a particular device 80 can be arranged with different numbers of turns, different dimensional spacing between adjacent coils 82c (where more than one coil is used) and/or other configurations. The circuit 60c can be configured to generate the device renderings based on tracking coil locations/positions relative to one another on a known device with a known shape and/or geometry or predictable or known changeable (deflectable) shape or form (e.g., deflectable end portion).

The circuit can identify or calculate the actual shape and orientation of the device for the renderings based on data from a CAD (computer aided design) model of the physical device. The circuit can include data regarding known or predictable shape behavior based on forces applied to the device by the body or by internal or external components and/or based on the positions of the different tracking coils in 3-D image space and known relative (dimensional) spacings.

As shown in FIG. 3, the display 20 can be provided in or associated with a clinician workstation 60 in communication with an MRI Scanner 10S. Other displays may be provided. The MRI Scanner 10S typically includes a magnet 15 in a shielded room and a control cabinet 11 (and other components) in a control room in communication with electronics in the magnet room. The MRI Scanner 10S can be any MRI Scanner as is well known to those of skill in the art.

Figure 4:
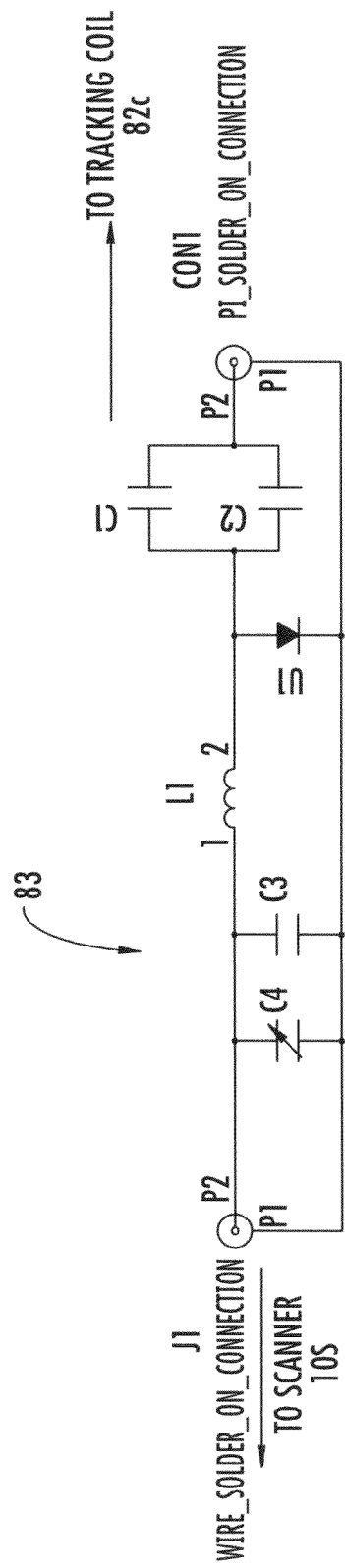
FIG. 4 is a circuit diagram of an exemplary tracking coil tuning circuit.

The tracking coils 82c can each include a tuning circuit that can help stabilize the tracking signal for faster system identification of spatial coordinates. FIG. 4 illustrates an example of a tuning circuit 83 that may be particularly suitable for a tracking coil 82c. As shown, CON1 connects the coaxial cable 81 to the tracking coil 82c on a distal end portion of the device 80 while J1 connects to the MR Scanner channel 10ch. The Scanner 10S sends a DC bias to the circuit 83 and turns U1 diode "ON" to create an electrical short which creates a high impedance (open circuit) on the tracking coil to prevent current flow on the tracking coil and/or better tracking signal (stability). The tuning circuit can be configured to have a 50 Ohm matching circuit (narrow band to Scanner frequency) to electrically connect the cable to the respective MR Scanner channel. When the diode U1 is open, the tracking coil data can be transmitted to the MR Scanner receiver channel 10ch. The C1 and C2 capacitors are large DC blocking capacitors. C4 is optional but can allow for fine tuning (typically between about 2-12 picofarads) to account for variability (tolerance) in components. It is contemplated that other tuning circuits and/or tracking signal stabilizer configurations can be used. The tuning circuit 83 can reside in the intrabody device 80 (such as in a handle (e.g., 440, FIG. 31) or other external portion), in a connector that connects the coil 82c to the respective MRI scanner channel 10ch, in the Scanner 10S, in an interface box 86 (FIG. 2), a patch panel 250 and/or the circuit 83 can be distributed among two or more of these or other components.

In some embodiments, each tracking coil 82c can be connected to a coaxial cable 81 having a length to the diode via a proximal circuit board (which can hold the tuning circuit and/or a decoupling/matching circuit) sufficient to define a defined odd harmonic/multiple of a quarter wavelength at the operational frequency of the MRI Scanner 10S, e.g., $\lambda/4$, $3\lambda/4$, $5\lambda/4$, $7\lambda/4$ at about 123.3 MHz for a 3.0T MRI Scanner. This length may also help stabilize the tracking signal for more precise and speedy localization. The tuned RF coils can provide stable tracking signals for precise localization, typically within about 1 mm or less. Where a plurality (e.g., two closely spaced) of adjacent tracking coils are fixed on a substantially rigid material, the tuned RF tracking coils can provide a substantially constant spatial difference with respect to the corresponding tracking position signals.

Additional discussion of tracking means and ablation catheters can be found in U.S. Pat. No. 6,701,176, and U.S. Provisional Application Ser. No. 61/261,103, the contents of which are hereby incorporated by reference as if recited in full herein. Exemplary catheters will be discussed further below.

FIGS. 5-8 illustrate a flexible (steerable) ablation catheter 80 having an ablation electrode, RF tracking coils, and a thermistor that can be electrically connected to an interface circuit of an MRI scanner by electrical lead assemblies of the present invention. The illustrated ablation catheter 80 includes an elongated flexible housing or shaft 402 having at least one lumen 404 (FIG. 7) therethrough and includes opposite distal and proximal end portions 406, 408, respectively. The distal end portion 406 includes an ablation tip 410 having an ablation electrode 410e (FIG. 6) for ablating target tissue. A pair of RF tracking coils individually identified as 412, 414, and which are equivalent to coils 82c of FIGS. 2-3, are positioned upstream from the ablation tip 410, as illustrated. The proximal end portion 408 of the catheter 80 is operably secured to a handle 440.

Figure 5:
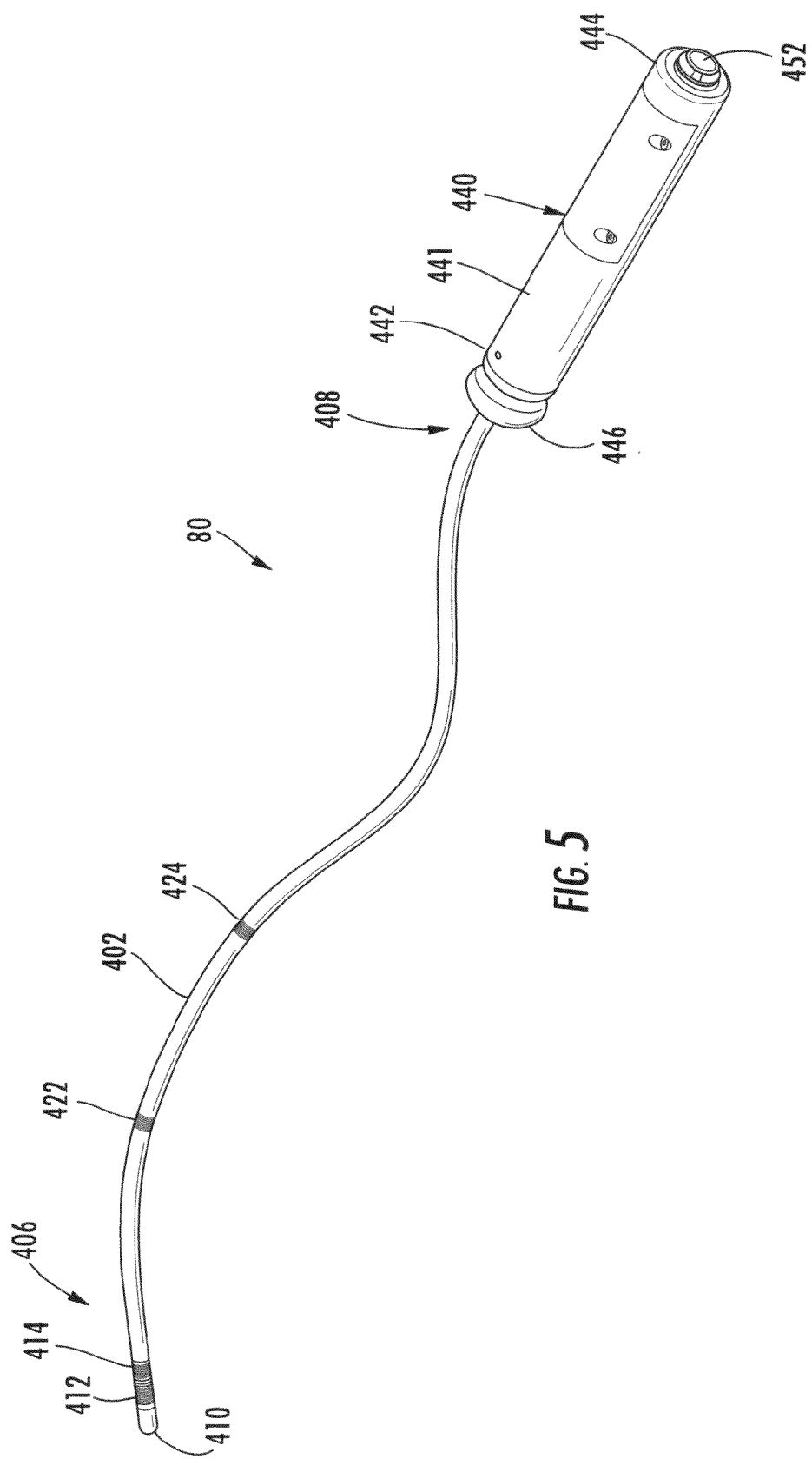
FIG. 5 is a perspective view of an exemplary ablation catheter in having an ablation electrode and RF tracking coils that can be electrically connected to an interface circuit of an MRI scanner by electrical lead assemblies of the present invention.
Figure 6:
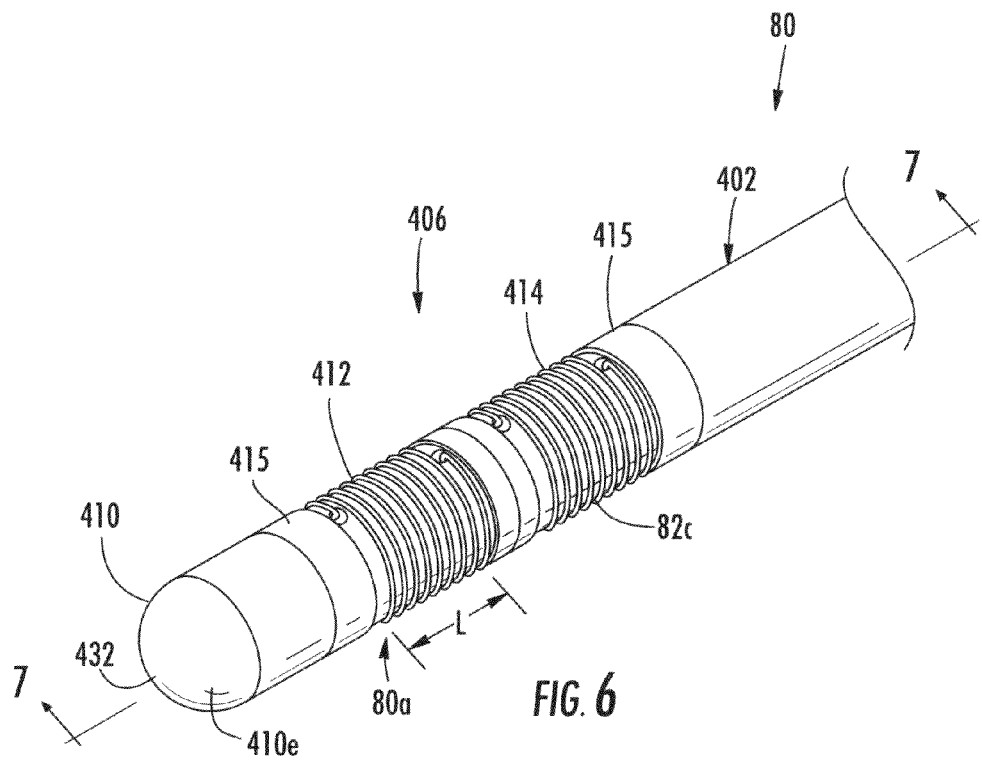
FIG. 6 is an enlarged partial perspective view of the tip portion of the ablation catheter of FIG. 5.
Figure 7:
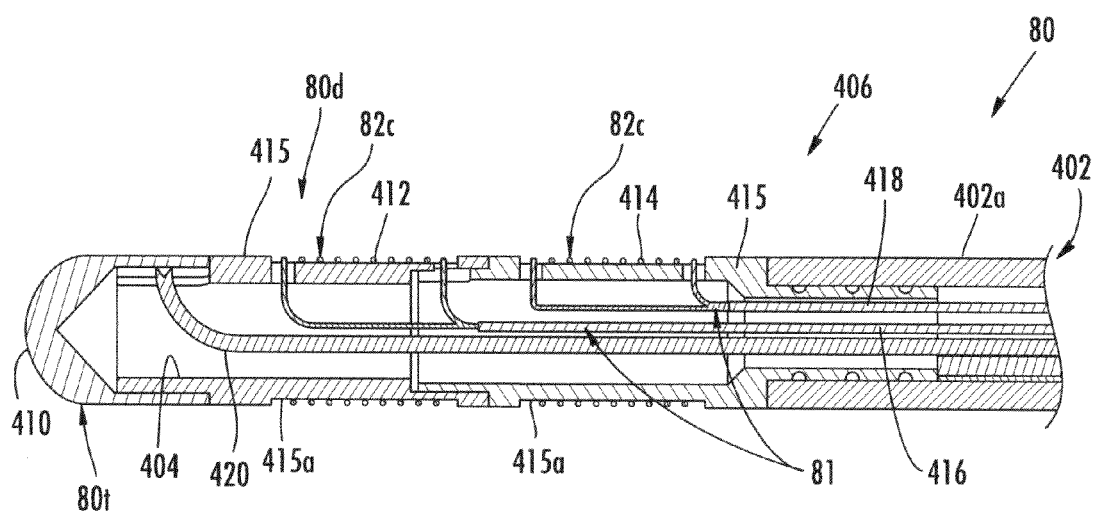
FIG. 7 is a cross-sectional view of the tip portion of the ablation catheter of FIG. 6 taken along lines 7-7.

FIG. 6 is an enlarged partial perspective view of the distal end portion 406 of the ablation catheter 80 of FIG. 5. The distal end portion 406 has an ablation tip 410 and two RF tracking coils 412, 414. The RF tracking coils 412, 414 are positioned upstream and adjacent the ablation tip 410 in spaced-apart relationship. The RF tracking coils 412, 414 are each electrically connected to a respective channel of an MRI scanner for tracking the location of the catheter 80 in 3-D space, via respective cables (e.g., coaxial cables) 416, 418 (FIG. 7) extending longitudinally through the catheter shaft lumen 404 and terminating at an electrical connector interface (450, FIG. 9) that is located, for example, in the handle 440.

In the illustrated embodiment, the ablation tip 410 includes an electrode 410e that is connected to an RF wire 420 (FIG. 8) that extends longitudinally within the lumen 404 to an electrical connector interface (450, FIG. 9), for example, within the handle 440 and that connects the ablation electrode 410e to an RF generator. The RF ablation electrode 410e is formed from an MRI-compatible conductive material capable of receiving RF energy and ablating tissue.

Figure 8:
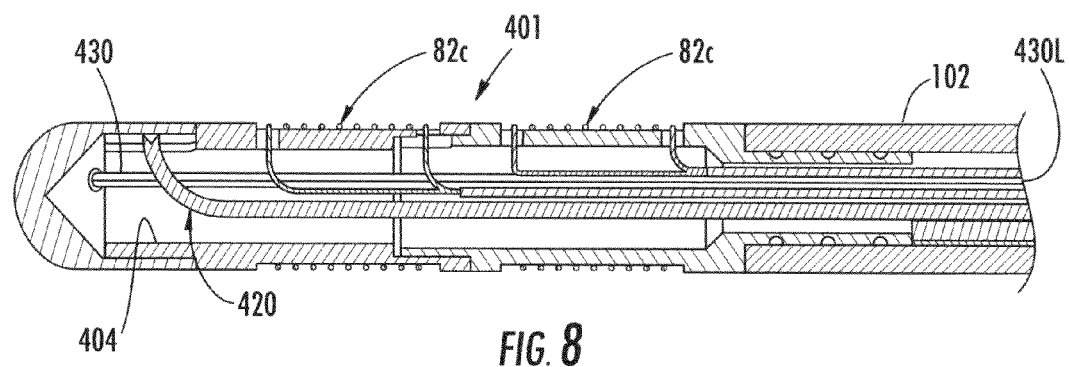
FIG. 8 illustrates the ablation catheter of FIG. 7 having a thermistor/thermocouple included therein with an electrical lead that extends longitudinally within the shaft lumen from the ablation tip to an electrical connector interface.

Referring to FIG. 8, the catheter 80 includes a thermistor 430 that has a lead 430L that extends longitudinally within the shaft lumen 404 from the ablation tip 410 to an electrical connector interface, typically at the proximal end of the ablation catheter, for example, in the handle 440 (FIG. 5). The thermistor 430 is configured to measure temperature at and/or adjacent to the ablation tip 410. The thermistor 430 can be configured to allow temperature to be monitored during ablation and/or at other times.

Figure 9:
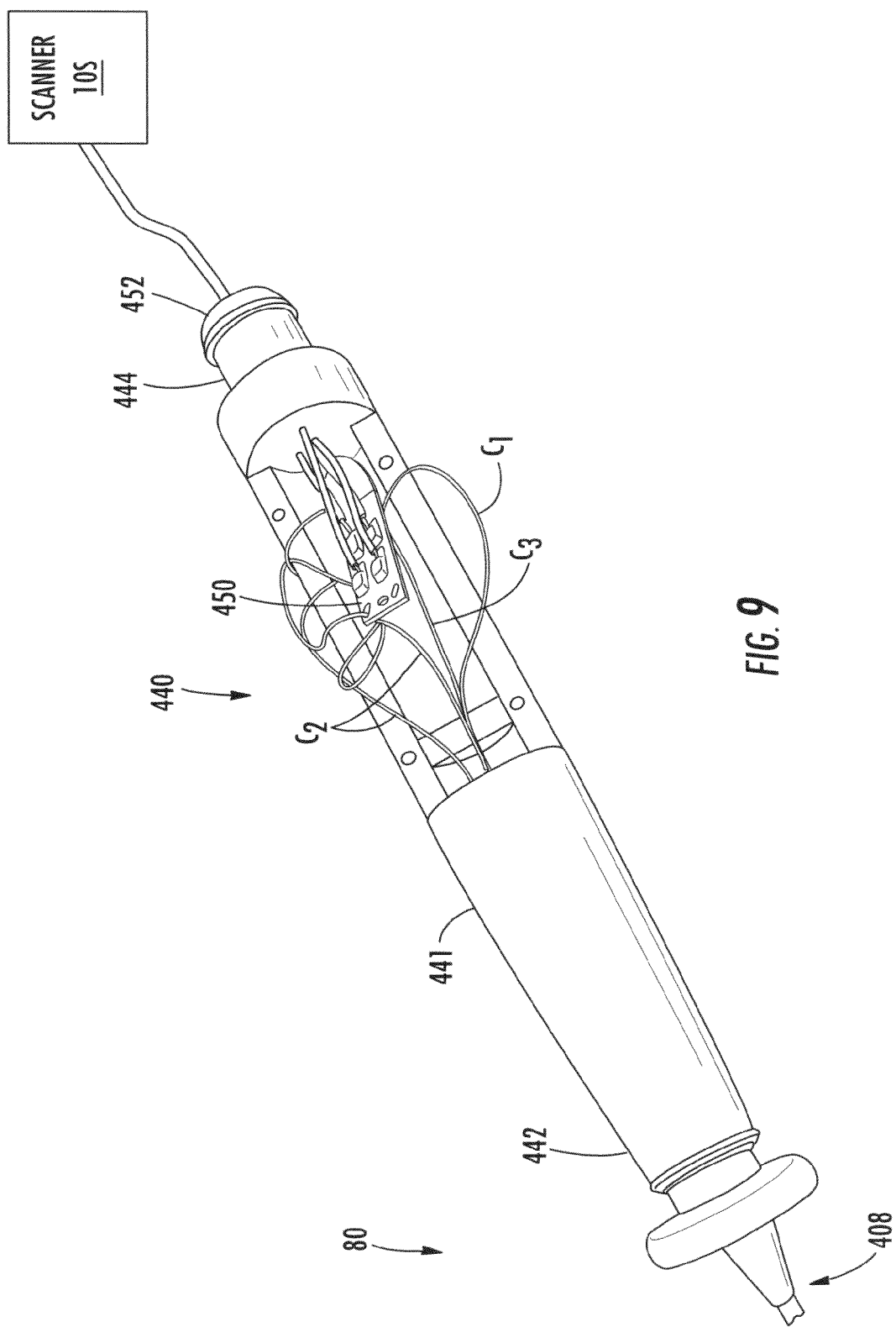
FIG. 9 is a perspective view of the handle at the proximal end of the ablation catheter of FIG. 5 with a cover removed and illustrating an exemplary MRI scanner interface circuit that can be connected by electrical lead assemblies of the present invention.

FIG. 9 is a perspective view of the handle 440 of the device 80 illustrated in FIG. 5. The handle 440 has a main body portion 441 with opposite distal and proximal end portions 442, 444. A cover (not shown) is removed from the handle main body portion 441 to illustrate the termination of the various conductors (i.e., from the RF tracking coils, ablation electrode, sensing electrodes, thermistor) extending into the handle 440 from the shaft lumen 404 at an electrical connector interface 450 (shown as PCB). Electrical connector interface 450 is electrically connected to an adapter 452 at the proximal end 444 of the handle 440. Adapter 452 is configured to receive one or more cables that connect the ablation catheter 80 to an MRI scanner 10S and that facilitate operation of the RF tracking coils 412, 414, 422, 424. Adapter 452 also is configured to connect the ablation tip 410 to an ablation source.

Figure 10A:
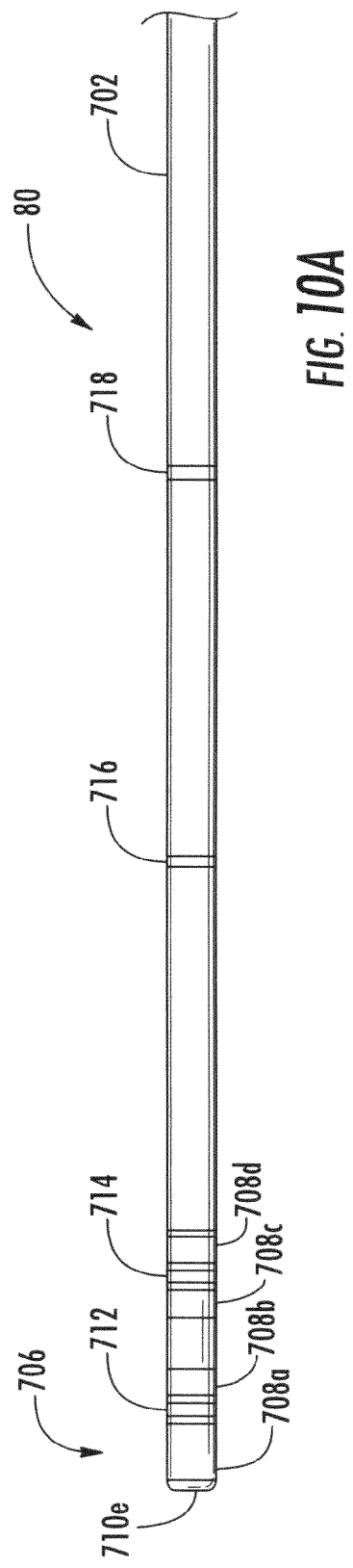
FIG. 10A is a partial side view of a distal end of an exemplary ablation catheter having an ablation electrode, RF tracking coils, and sensing electrodes that can be electrically connected to an interface circuit of an MRI scanner by electrical lead assemblies of the present invention.
Figure 10B:
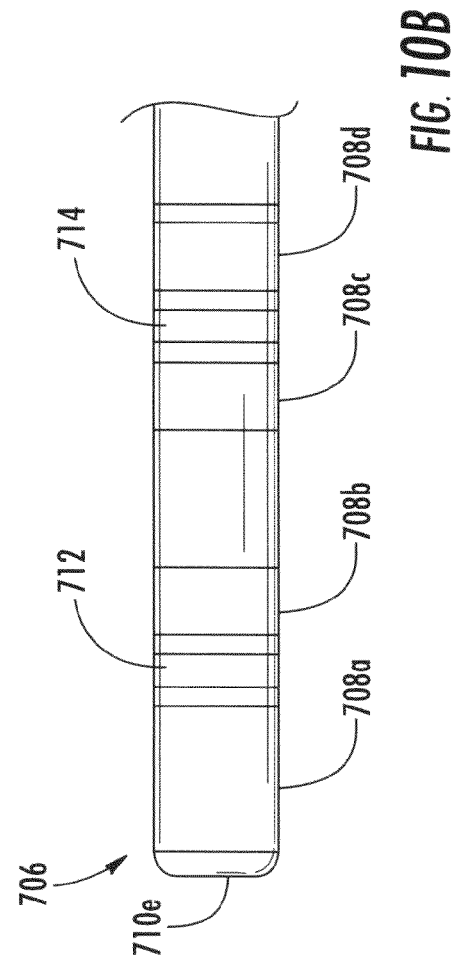
FIG. 10B and an enlarged partial view of the distal end of the ablation catheter of FIG. 10A.

FIGS. 10A-10B illustrate a flexible (steerable) ablation catheter 80 having an ablation electrode 710e, RF tracking coils 712, 714, 716, 718, and sensing electrodes 708a-708d that can be electrically connected to an interface circuit of an MRI scanner by electrical lead assemblies of the present invention. The illustrated ablation catheter 80 includes an elongated flexible housing or shaft 702 with opposite distal and proximal end portions, only the distal end portion 706 is illustrated. The proximal end portion of the catheter 80 is operably secured to a handle, as is well known. The distal end portion 706 includes a plurality of electrodes 708a-708d for sensing local electrical signals or properties arranged in spaced-apart relationship, as illustrated. The RF tracking coils 712, 714, 716, 718 are equivalent to coils 80c in FIGS. 2-3 and coils 412, 414, 422, 424 in FIG. 5. Tracking coil 712 is positioned between the first and second electrodes 708a, 708b, and tracking coil 714 is positioned between the third and fourth electrodes 708c, 708d, as illustrated.

Figure 11:
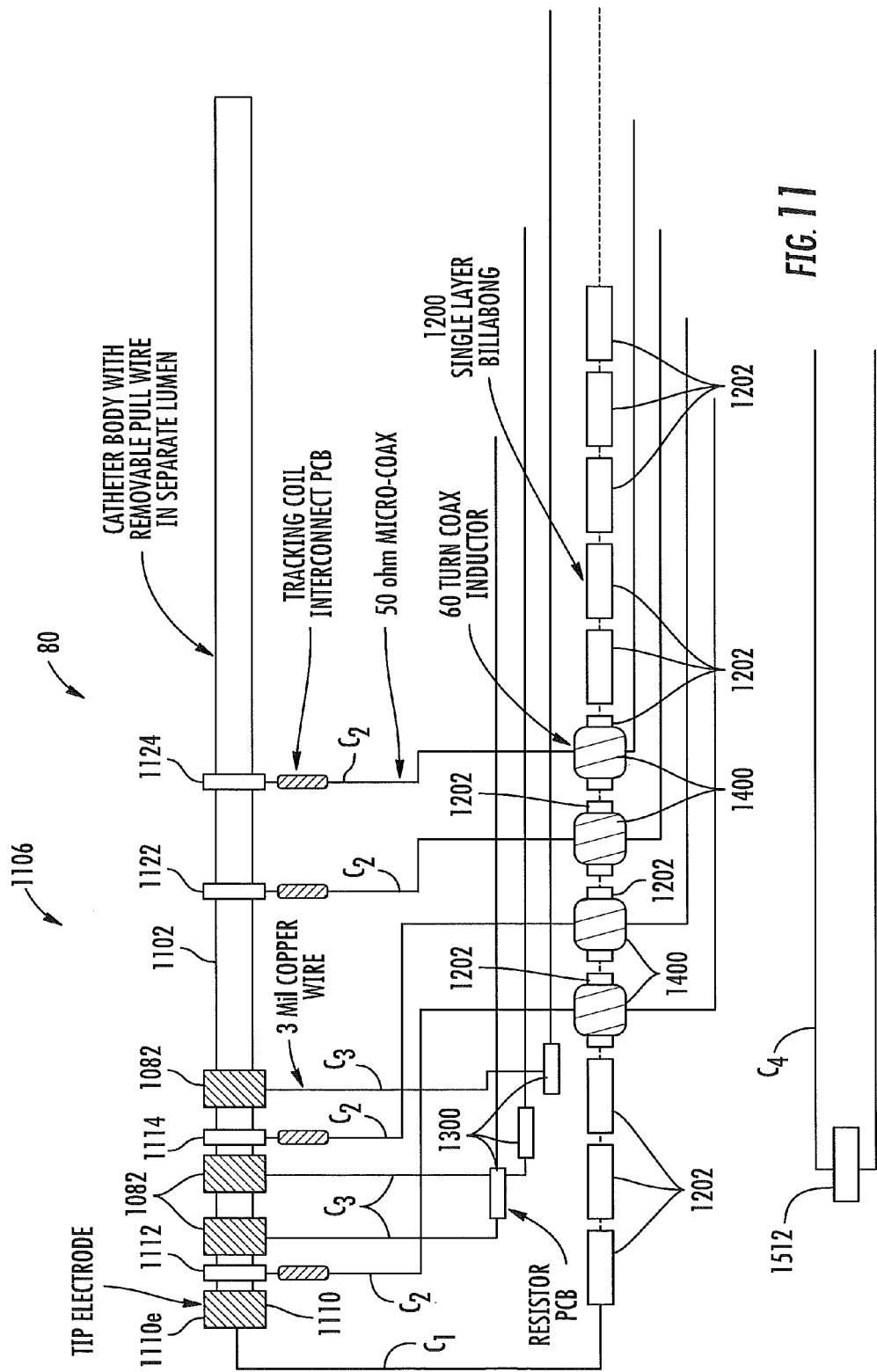
FIG. 11 is a schematic illustration of an exemplary ablation catheter having an ablation electrode, RF tracking coils, and sensing electrodes that can be electrically connected to an interface circuit of an MRI scanner by electrical lead assemblies of the present invention.

FIG. 11 is a schematic illustration of the distal end portion 1106 of an ablation catheter 80 that includes an ablation tip 1110 having an ablation electrode 1110e (equivalent to 410e of FIG. 6 and 710e of FIGS. 10A-10B) for ablating target tissue, RF tracking coils 1112, 1114, 1122, 1124 (equivalent to coils 80c in FIGS. 2-3, coils 412, 414, 422, 424 in FIG. 5, and coils 712, 714, 716, 718 in FIGS. 10A-10B), EGM (electrogram) sensing electrodes 1082 (equivalent to electrodes 708a-708d in FIGS. 10A-10B) positioned between the first and second tracking coils 1112, 1114, a sensing electrode 1082 positioned between the tracking coil 1114 and the tracking coil 1122, and a thermistor 1512. A conductor $C_1$ connects the ablation electrode 1110e to an RF generator. Electrical conductors (e.g., coaxial cables) $C_2$ connect the tracking coils 1112, 1114, 1122, 1124 to the electrical interface (e.g., 450, FIG. 9) of an MRI scanner, electrical conductors $C_3$ connect the sensing electrodes 1082 to the electrical interface, and electrical connector $C_4$ connects the thermistor 1512 to the electrical interface, as described above.

As described above, the ablation electrode 1110e delivers RF energy to tissue to cause thermal ablation of tissue. The sensing electrodes 1082 are utilized to measure cardiac potentials. The thermistor 1512 is utilized to measure the temperature of the ablation electrode 1110e and/or temperature of local tissue. The RF tracking coils 1112, 1114, 1122, 1124 generate NMR signals so that the MRI scanner can obtain location information of the one or more coils in a 3D MRI space. These electrodes, thermistors and tracking coils are connected by various conductors $C_1$-$C_4$.

Referring to FIGS. 12A-12B, 13A-13D, 14A-14D, 15A-15B, and 16A-16B, various electrical lead assemblies that can be formed from the conductors $C_1$-$C_4$ of FIG. 11 and that can attenuate RF coupling and local temperature rise are illustrated. FIG. 12A illustrates an electrical lead subassembly 1500 having conductors connected to an ablation electrode 1110e, one or more sensing electrodes 1082, and a thermistor 1512 of an MRI-compatible ablation catheter (e.g., 80, FIG. 5), according to some embodiments of the present invention. The electrical lead subassembly 1500 includes a first insulated conductor $C_1$, multiple second insulated conductors $C_3$, and a third insulated conductor $C_4$. As shown in FIG. 12B, conductor $C_1$ has a series of alternating single layer coil sections $C_{1a}$ and multi-layer coil sections $C_{1b}$. Conductor $C_1$ is connected at one end to the ablation electrode 1110e and to an electrical interface (e.g., 450, FIG. 9) at the opposite end, as described above. In some embodiments, conductor $C_1$ may include a plurality of individually insulated conductors, and may be co-wound insulated conductors. Conductor $C_1$ can have low resistivity to carry high current for ablation. The multi-layer sections $C_{1b}$ of conductor $C_1$ can be adjusted such that they have an impedance of higher than 50 ohms/cm at NMR frequency. The impedance of each multilayer section $C_{1b}$ is a function of pitch (number of co-wound conductors), length of the multi-layer coil section and diameter of the coil and conductors.

As illustrated in FIG. 12A, each conductor $C_3$ is connected at one end to a respective sensing electrode 1082 and at an opposite end to an electrical interface (e.g., 450, FIG. 9), as described above. The conductor $C_4$ is connected at one end to a thermistor 1512 and at an opposite end to the electrical interface (e.g., 450, FIG. 9). In some embodiments, each conductor $C_3$ may include a plurality of individually insulated conductors, and may be co-wound insulated conductors. Similarly, conductor $C_4$ may include a plurality of individually insulated conductors, and may be co-wound insulated conductors. As shown, each conductor $C_3$ has a respective series of alternating single layer coil sections $C_{3a}$ and multi-layer coil sections $C_{3b}$ (e.g., typically tri-layer configurations). Similarly, conductor $C_4$ has a respective series of alternating single layer coil sections $C_{4a}$ and multi-layer coil sections $C_{4b}$. The multi-layer sections $C_{3b}$ of each conductor $C_3$ can be adjusted such that they have a selected impedance (e.g., an impedance greater than 50 ohms/cm at an NMR frequency). Similarly, the multi-layer sections $C_{4b}$ of conductor $C_4$ can be adjusted such that they have a selected impedance (e.g., an impedance greater than 50 ohms/cm at an NMR frequency).

As illustrated in FIG. 12A, each multi-layer coil section $C_{3b}$ of each conductor $C_3$ is coiled around a respective single layer coil section $C_{1a}$ of conductor $C_1$ and each single layer coil section $C_{3a}$ of each conductor $C_3$ is coiled around a respective multi-layer coil section $C_{1b}$ of conductor $C_1$. Similarly, each multi-layer coil section $C_{4b}$ of conductor $C_4$ is coiled around a respective single layer coil section $C_{1a}$ of conductor $C_1$ and each single layer coil section $C_{4a}$ of conductor $C_4$ is coiled around a respective multi-layer coil section $C_{1b}$ of conductor $C_1$. This configuration allows the electrical lead subassembly 1500 to have a substantially constant diameter $D_1$ along this segment (typically the entire length), as illustrated.

Each of the multi-layer coil sections $C_{1b}$, $C_{3b}$, $C_{4b}$ serves as a respective current suppression module (CSM) and can have an impedance greater than about 50 ohms per centimeter at a nuclear magnetic resonance (NMR) operating frequency of an MRI scanner. In some embodiments, each of the multi-layer coil sections $C_{1b}$, $C_{3b}$, $C_{4b}$ have three layers of windings. For example, each multi-layer coil section $C_{1b}$, $C_{3b}$, $C_{4b}$ includes a first coiled layer that extends in a first lengthwise direction for a first physical length, a second coiled layer coiled around the first coiled layer in a substantially opposing lengthwise direction for a second physical length, and a third coiled layer coiled around the second coiled layer in the first lengthwise direction for a third physical length. In some embodiments, the first layer may be coiled left to right, the second layer coiled right to left on top of the first layer, and the third layer may be coiled left to right on top of the first and second layers. The coils in the first, second and third layers may have the same pitch or may have a different pitch. See, for example, PCT Publication No. WO 2008/115383 entitled "Methods and Apparatus for Fabricating Leads with Conductors and Related Flexible Lead Configurations", which is incorporated herein by reference in its entirety.

Referring now to FIGS. 13A-13D, a second electrical lead subassembly 1502 configured to be attached to one or more catheter RF tracking coils 1112, 1114, 1122, 1124 is illustrated. The second electrical lead subassembly 1502 includes a separate conductor (or separate plurality of conductors) $C_2$ for each respective RF tracking coil. For example, FIG. 13A illustrates the second electrical lead subassembly 1502 for a single RF tracking coil 1112, FIG. 13B illustrates the second electrical lead subassembly 1502 for two RF tracking coils 1112, 1114, FIG. 13C illustrates the second electrical lead subassembly 1502 for three RF tracking coils 1112, 1114, 1122, and FIG. 13D illustrates the second electrical lead subassembly 1502 for four RF tracking coils 1112, 1114, 1122, 1124. Each conductor $C_2$ includes at least one coiled section $C_{2a}$ typically configured to have a complex impedance of greater than, for example, 100 ohms at the NMR frequency, although other impedance values can be obtained. Conductor $C_2$ may be one or more coaxial cables or one or more twisted wire pairs.

Depending on the overall length of the second electrical lead subassembly 1502, each conductor $C_2$ may have one or more coiled sections $C_{2a}$. Typically the length of each coiled section $C_{2a}$ is about a quarter (¼) wavelength at the NMR frequency. In the illustrated embodiments of FIGS. 13A-13D, each conductor $C_2$ includes a plurality of spaced-apart coiled sections $C_{2a}$. Also as illustrated in FIGS. 13B-13D, if two or more RF tracking coils are utilized, the respective conductors $C_2$ of the different RF tracking coils are arranged such that the coiled sections $C_{2a}$ are in adjacent, axial relationship with each other. As illustrated in FIGS. 13A-13D, the straight sections $C_{2b}$ of the conductors $C_2$ are positioned to the outside of each coiled section $C_{2a}$.

In the illustrated embodiment of FIGS. 13A-13D, the coils in each coiled section $C_{2a}$ are wound left to right. However, embodiments of the present invention are not limited to the illustrated configuration of FIGS. 13A-13D. For example, as illustrated in FIGS. 14A-14D, the coils in each coiled section $C_{2a}$ can be wound right to left. In the embodiment of FIGS. 14A-14D, each conductor $C_2$ has a straight forward section $C_{2b}$ followed by a coiled back section (i.e., coiled section $C_{2a}$ that is wound right to left) followed by another forward straight section $C_{2b}$. The impedance of this configuration (i.e., the first straight forward section, the coiled back section, and the second straight forward section) may be, for example, higher than 100 ohms at the NMR frequency. However, the impedance of this configuration may have other values as well. For example, the impedance of this configuration may be, for example, higher than 50 ohms at the NMR frequency, higher than 200 ohms at the NMR frequency, etc.

Figure 15A:
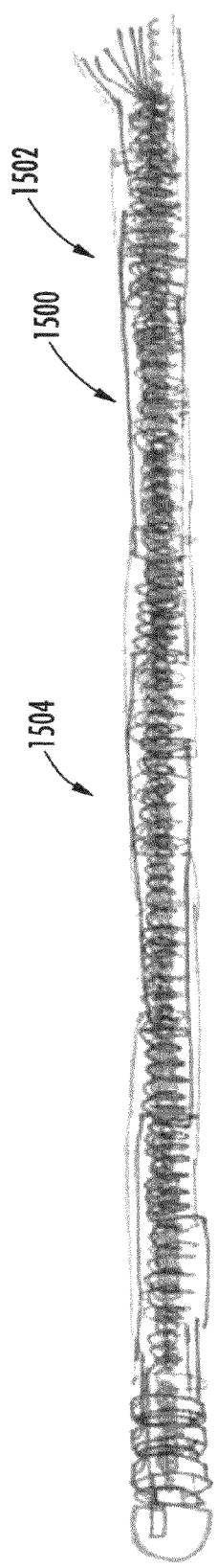
FIG. 15A is a schematic color illustration of an electrical lead assembly according to some embodiments of the present invention that includes the electrical lead subassembly of FIG. 12A inserted within the electrical lead subassembly of FIG. 13D.
Figure 15B:
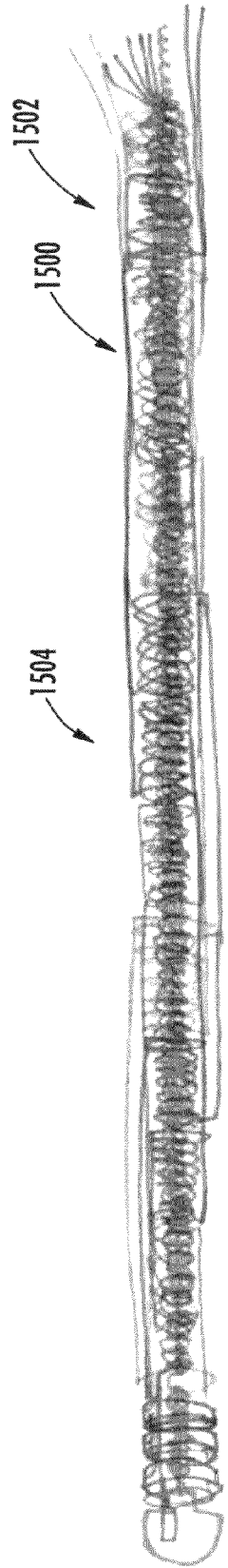
FIG. 15B is a schematic color illustration of an electrical lead assembly according to some embodiments of the present invention that includes the electrical lead subassembly of FIG. 12A inserted within the electrical lead subassembly of FIG. 14D.

The inner diameter $D_i$ of the coiled sections $C_{2a}$ in FIGS. 13A-13D and FIGS. 14A-14D is larger than the outer diameter $D_1$ of the first electrical lead subassembly 1500 of FIG. 12A. This is such that the electrical lead subassembly 1500 of FIG. 12A can be inserted within the coiled sections of the second electrical lead subassembly 1502 to form electrical lead assembly 1504, as illustrated in FIGS. 15A and 15B. In FIG. 15A, the second electrical lead subassembly 1502 has the configuration of FIG. 13D (i.e., with the coils in each coiled section $C_{2a}$ wound left to right). In FIG. 15B, the second electrical lead subassembly 1502 has the configuration of FIG. 13D (i.e., with the coils in each coiled section $C_{2a}$ wound right to left).

Referring to FIG. 16A, an elongate electrical lead subassembly 1500' for an MRI-compatible medical device, such as an ablation catheter, according to other embodiments of the present invention is illustrated. The illustrated electrical lead subassembly 1500' is an alternative to the subassembly 1500 of FIG. 12A. The illustrated subassembly 1500' includes a conductor $C_1$ that is connected to an ablation electrode 1110e, multiple conductors $C_3$ that are connected to respective sensing electrodes 1082, and a conductor $C_4$ that is connected to a thermistor 1512. As illustrated in FIG. 16B, the conductor $C_1$ has first and second multi-layer coil sections $C_{1b}$ with a single layer coil section $C_{1a}$ therebetween. The conductors $C_3$ and $C_4$ each have a multi-layer coil section $C_{3b}$, $C_{4b}$ that is coiled around the single layer coil section $C_{1a}$ of the conductor C1. This configuration allows the electrical leas subassembly 1500' to have a substantially constant diameter $D_1$ along this segment length (typically substantially the entire length), as illustrated.

In the drawings and specification, there have been disclosed embodiments of the invention and, although specific terms are employed, they are used in a generic and descriptive sense only and not for purposes of limitation, the scope of the invention being set forth in the following claims. Thus, the foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. An elongate electrical lead subassembly, comprising:
   at least one first conductor comprising a series of alternating single layer coil sections and multi-layer coil sections and attached at one end portion to an ablation electrode; and
   at least one second conductor comprising a series of alternating single layer coil sections and multi-layer coil sections and attached at one end portion to a sensing electrode upstream of the ablation electrode;
   wherein each multi-layer coil section of the at least one second conductor is coiled around a respective single layer coil section of the at least one first conductor, and wherein each single layer coil section of the at least one second conductor is coiled around a respective multi-layer coil section of the at least one first conductor such that the electrical lead assembly has a substantially constant diameter along at least a portion of its length.

2. The electrical lead subassembly of claim 1, wherein the at least one first conductor and the at least one second conductor are insulated.

3. The electrical lead subassembly of claim 1, wherein the multi-layer coil sections of the at least one first conductor and the at least one second conductor comprise a first coiled layer that extends in a first lengthwise direction for a first physical length, a second coiled layer coiled around the first coiled layer in a substantially opposing lengthwise direction for a second physical length, and a third coiled layer coiled around the second coiled layer in the first lengthwise direction for a third physical length.

4. The electrical lead subassembly of claim 1, wherein the multi-layer coil sections of the at least one first conductor and the at least one second conductor have an impedance greater than about 50 ohms per centimeter at a nuclear magnetic resonance (NMR) operating frequency of an MRI scanner.

5. The electrical lead subassembly of claim 1, wherein the at least one first and second conductors each comprise at least one coaxial cable.

6. An elongate electrical lead assembly, comprising:
   a first elongate electrical lead subassembly comprising at least one conductor having a series of alternating single layer coil sections and multi-layer coil sections and attached at one end portion to an ablation electrode;
   a second elongate electrical lead subassembly comprising at least one conductor having a series of alternating single layer coil sections and multi-layer coil sections and attached at one end portion to an electrode upstream of the ablation electrode;

wherein each multi-layer coil section of the second electrical lead subassembly is coiled around a respective single layer coil section of the first electrical lead subassembly, and wherein each single layer coil section of the second electrical lead subassembly is coiled around a respective multi-layer coil section of the first electrical lead subassembly; and a third elongate electrical lead subassembly comprising at least one conductor having a coiled section that coaxially surrounds the first and second electrical leads and attached at one end portion to an RF tracking coil.

7. The electrical lead assembly of claim 6, wherein the third electrical lead subassembly comprises a plurality of conductors, and wherein the coiled sections of the conductors are in adjacent, axial relationship with each other.

8. The electrical lead assembly of claim 6, further comprising a fourth electrical lead subassembly having a series of alternating single layer coil sections and multi-layer coil sections, wherein each multi-layer coil section of the fourth electrical lead subassembly is coiled around a respective single layer coil section of the first electrical lead subassembly, wherein each single layer coil section of the fourth electrical lead subassembly is coiled around a respective multi-layer coil section of the first electrical lead subassembly, and wherein one end portion of the fourth electrical lead subassembly is attached to a thermistor.

9. The electrical lead assembly of claim 6, wherein the multi-layer coil sections of the first and second electrical lead subassemblies each comprise a first coiled layer that extends in a first lengthwise direction for a first physical length, a second coiled layer coiled around the first coiled layer in a substantially opposing lengthwise direction for a second physical length, and a third coiled layer coiled around the second coiled layer in the first lengthwise direction for a third physical length.

10. The electrical lead assembly of claim 6, wherein the multi-layer coil sections of the first and second electrical lead subassemblies have an impedance greater than about 50 ohms per centimeter at a nuclear magnetic resonance (NMR) operating frequency of an MRI scanner.

11. A MRI-compatible medical device, comprising:
an elongated flexible shaft having a distal end portion, and an opposite proximal end portion;
an electrical connector interface proximate the proximal end portion;
an ablation electrode at the flexible shaft distal end portion;
a first elongate electrical lead that extends longitudinally within the flexible shaft, wherein the first electrical lead comprises at least one conductor and has opposing proximal and distal end portions, wherein the first electrical lead distal end portion is connected to the ablation electrode, wherein the first electrical lead proximal end is connected to the electrical connector interface, and wherein the first electrical lead comprises a series of alternating single layer coil sections and multi-layer coil sections;
at least one sensing electrode at the shaft distal end portion; and
a second elongate electrical lead that extends longitudinally within the flexible shaft, wherein the second electrical lead comprises at least one conductor and has opposing proximal and distal end portions, wherein the second electrical lead distal end portion is connected to the at least one sensing electrode, wherein the second electrical lead proximal end is connected to the electrical connector interface, and wherein the second electrical lead comprises a series of alternating single layer coil sections and multi-layer coil sections;
wherein each multi-layer coil section of the second electrical lead is coiled around a respective single layer coil section of the first electrical lead, and wherein each single layer coil section of the second electrical lead is coiled around a respective multi-layer coil section of the first electrical lead.

12. The medical device of claim 11, wherein the at least one conductors of the first and second electrical leads are insulated.

13. The medical device of claim 11, wherein the multi-layer coil sections of the first and second electrical leads comprise a first coiled layer that extends in a first lengthwise direction for a first physical length, a second coiled layer coiled around the first coiled layer in a substantially opposing lengthwise direction for a second physical length, and a third coiled layer coiled around the second coiled layer in the first lengthwise direction for a third physical length.

14. The medical device of claim 11, wherein the multi-layer coil sections of the first and second electrical leads have an impedance greater than about 50 ohms per centimeter at a nuclear magnetic resonance (NMR) operating frequency of an MRI scanner.

15. The medical device of claim 11, wherein the first electrical lead at least one conductor comprises at least one coaxial cable, and wherein the second electrical lead at least one conductor comprises at least one coaxial cable.

16. The medical device of claim 11, further comprising:
at least one RF tracking coil positioned at the distal end portion of the flexible shaft; and
a third elongate electrical lead that extends longitudinally within the flexible shaft, wherein the third electrical lead comprises at least one conductor and has opposing proximal and distal end portions, wherein the third electrical lead distal end portion is connected to the at least one RF tracking coil, wherein the third electrical lead proximal end is connected to the electrical connector interface, and wherein the third electrical lead comprises a first coiled section that coaxially surrounds the first and second electrical leads.

17. The medical device of claim 16, wherein the at least one RF tracking coil comprises a plurality of RF tracking coils, and wherein the third electrical lead at least one conductor comprises a respective plurality of conductors having coiled sections in adjacent, axial relationship with each other.

18. The medical device of claim 11, further comprising:
a thermistor positioned adjacent the distal end portion of the flexible shaft; and
a fourth electrical lead that extends longitudinally within the flexible shaft, wherein the fourth electrical lead comprises at least one conductor and has opposing proximal and distal end portions, wherein the fourth electrical lead distal end portion is connected to the thermistor, wherein the fourth electrical lead proximal end is connected to the electrical connector interface, and wherein the fourth electrical lead comprises a series of alternating single layer coil sections and multi-layer coil sections;
wherein each multi-layer coil section of the fourth electrical lead is coiled around a respective single layer coil section of the first electrical lead, and wherein each single layer coil section of the fourth electrical lead is coiled around a respective multi-layer coil section of the first electrical lead.

19. An elongate electrical lead assembly, comprising:
at least one first conductor having first and second multi-layer coil sections with a single layer coil section therebetween, wherein the first multi-layer coil section has a length greater than a length of the second multi-layer coil section and greater than a length of the single layer coil section; and
at least one second conductor having at least one multi-layer coil section, wherein the at least one multi-layer coil section of the at least one second conductor is coiled around the single layer coil section of the at least one first conductor.

20. The electrical lead assembly of claim 19, further comprising at least one third conductor having a coiled section that coaxially surrounds the first and second at least one conductors.

21. The electrical lead assembly of claim 20, wherein the at least one third conductor comprises a plurality of conductors, and wherein the coiled sections of the conductors are in adjacent, axial relationship with each other.

22. The electrical lead assembly of claim 19, further comprising at least one fourth conductor having at least one multi-layer coil section, wherein the at least one multi-layer coil section of the at least one fourth conductor is coiled around the single layer coil section of the at least one first conductor.

23. The electrical lead assembly of claim 19, the at least one multi-layer coil section of the at least one second conductor comprises a plurality of adjacent multi-layer coil sections each comprising a first coiled layer that extends in a first lengthwise direction for a first physical length, a second coiled layer coiled around the first coiled layer in a substantially opposing lengthwise direction for a second physical length, and a third coiled layer coiled around the second coiled layer in the first lengthwise direction for a third physical length.

* * * * *